Sept. 7, 1937. R. K. CUTTER Re. 20,495

HYPODERMIC SYRINGE

Original Filed July 21, 1930

INVENTOR.
Robert K. Cutter.
BY
Townsend and Loftus.
ATTORNEYS.

Reissued Sept. 7, 1937 Re. 20,495

UNITED STATES PATENT OFFICE 20,495

HYPODERMIC SYRINGE

Robert K. Cutter, Berkeley, Calif., assignor to Cutter Laboratories, Berkeley, Calif., a corporation of California Original No. 1,948,982, dated February 27, 1934, Serial No. 628,790, August 15, 1932, which is a continuation of application July 21, 1930, Serial No. 469,447. This application for reissue February 3, 1936, Serial No. 62,162

2 Claims. (Cl. 128—218)

This application is a continuation of my application Serial No. 469,447, filed July 21, 1930, for "Hypodermic syringe."

This invention relates to improvements in the construction of hypodermic syringes particularly designed for use in connection with the storage, transportation, preservation and application of biological and similar products which are stored, transported, preserved or dispensed in syringe containers.

Objects of the present invention are generally to improve and simplify the construction and operation of devices of the character described; to provide a syringe charged with the medicine to be injected and which may function as a storage container but not permit leakage of the medicine from the front to the rear of the plunger even when subjected to vibration such as occurs during transit; to provide an improved type of piston or plunger which will not permit leakage from the front to the back thereof; to provide an improved piston or plunger which will not jam when pushed forward to eject the medicine from the syringe; to provide a piston or plunger which will permit a greater tolerance between the outer surface thereof and the inner surface of the cylinder or barrel in which it is used; to provide a plunger which is adapted to be constructed entirely of a resilient material such as rubber or the like; other objects being apparent from a reading of the appended description taken in connection with the accompanying drawing which illustrates the invention. In such drawing—

Figure 1:
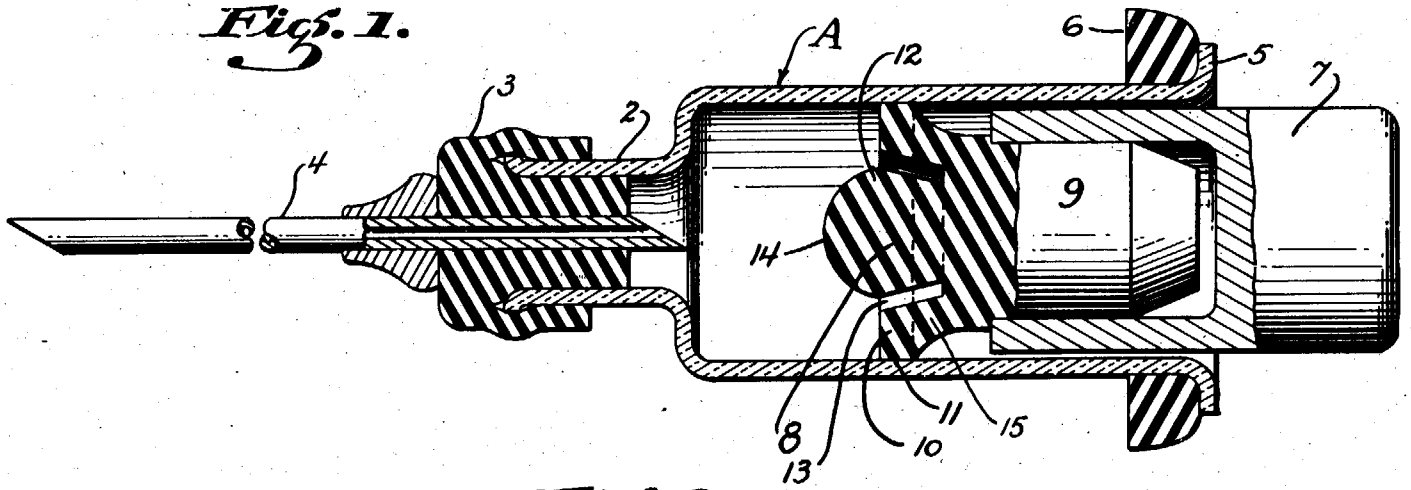
Figure 1 is a central longitudinal section through the syringe.
Figure 2:
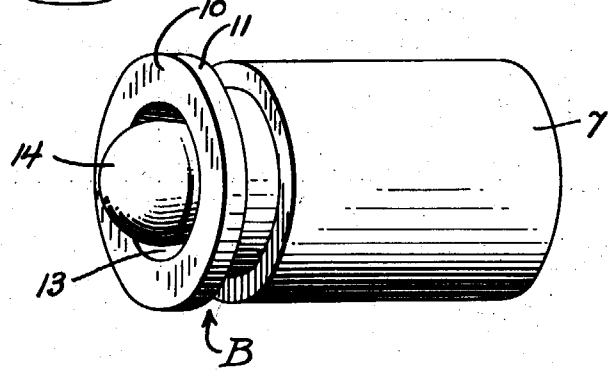
Figure 2 is a perspective view of the plunger showing the operating handle attached thereto.

Referring to the drawing in detail and particularly Figure 1, A indicates a cylinder or barrel which in this instance is preferably constructed of glass, although it may be made of any suitable material. The discharge end of the cylinder is reduced in diameter to form a neck 2 in which is inserted a rubber sealing plug 3 and this is in turn designed to receive a hollow needle 4 through which the serum is discharged.

The opposite end of the cylinder or barrel is open and provided with a flange 5 and this is protected by means of an annular rubber ring 6 which functions as a finger grip. Adapted to be inserted in the cylinder or barrel A is a combination plunger and sealing plug generally indicated at B and for suitable attachment thereto I provide an operating handle 7. The plunger consists of a head member 8, one end of which terminates in a shank-like extension 9 which is adapted to receive the operating handle. The periphery of the head terminates in an annular flange or ring 10 which forms the contact member of the plunger, and the exterior surface 11 of this member forms a snug fit with relation to the inner surface of the barrel. The head member 8 also carries a plug or filler member 12 and there is an annular groove or space 13 formed between said plug and contact ring 10 to permit free expansion and contraction thereof. The annular groove 13 should be of substantially greater depth than the contacting surface 11, while the width of this groove may be sufficient to admit liquid so that a pressure will be exerted on the walls thereof when forward movement is imparted to the plunger during discharge of the medicine; while that part 10 comprised between the annular groove 13 and the exterior surface 11 (taken on a cross section) should be of sufficient thickness to make and maintain a good contact with the inner surface of the barrel in order to prevent sufficient yielding to permit passage of liquid from ahead of the plunger to points therebehind, such thickness being determined with a consideration of the softness and flexibility and possibly other characteristics of the material of which the plunger is made. This part between the annular groove 13 and the outer periphery is so made that it normally tends to have an outer periphery slightly greater than the inner periphery of the barrel. The projection 14 serves only to reduce the residual syringe contents to a minimum and is here shaped to fit the syringe neck as closely as possible. It will, of course, be modified in shape to fit the neck of any syringe and it can be entirely eliminated, if desired, in which case a depression or well is formed within the annular contact ring 10.

The plunger as a whole will preferably be constructed of soft rubber or a similar material and in actual operation it will be inserted in the open end of the barrel after the barrel has been sterilized. The barrel is then filled with serum through the neck and the plug prevents escape, leakage, or contamination of the serum content. Products such as diphtheria anti-toxin, tetanus anti-toxin, as well as many other products, may be sold and transported in, and served to the patient from, syringes comprising my new invention. Some of these products are necessary for the saving of human life, but it often happens that a physician will carry necessary products for many miles to the patient only to find that on arrival a substantial part of the medicine has leaked beyond the plunger and has become dried and un-usable, and this is one of the disadvantages, and it is a very great one, which has in practical use been obviated by my invention. Now, when the syringe is to be employed, end pressure is applied to the operating handle and the plunger will then be forced inwardly and during such movement will discharge the serum through the hollow needle. During such inward movement pressure is applied to the liquid and, as this enters the annular groove 13 formed between the filler plug 12 and the contact ring 10, an outward pressure is exerted on the inner face of the contact ring, thus forcing the contact face 11 into snug engagement with the inner surface of the barrel and insuring complete discharge of the serum content.

Furthermore, when the plunger is forced inwardly by means of the operating handle the plunger as a whole tends to slightly compress due to frictional resistance and this compressing action further assists in maintaining a snug engagement between the plunger and the barrel.

While the plunger mechanism illustrated in this instance is primarily intended for antitoxin syringes which are filled with a single charge and which are discarded after first use, it is obvious that the plunger may be employed in connection with permanent syringes and like devices. In that case the shank or extension 9 may be provided with molded threads or the like so that it may be readily connected with a rod or any other plunger operating mechanism of suitable construction.

In actual practice, the annular ring 10 of the plunger is sufficiently resilient to expand by compression, friction and by the application of pressure, while due to its resiliency it may be contracted or forced inwardly when inserted into a barrel, while said part 10 is sufficiently strong to maintain a position against the inner surface of the barrel which will prevent rearward movement of the medicine therepast. A plunger thus constructed permits a greater tolerance between the plunger and the inner surface of the barrel than is usually possible with ordinary plungers. The plunger structure, accordingly, has several advantages, to-wit, it will function both as a plunger and as a sealing plug. Due to the tolerance permitted, it will fit a greater number of cylinders of varying size with less tendency to leakage or sticking. It is contractible and it is also automatically expansible when pressure or friction is applied and, as it is constructed of rubber, it may be molded or otherwise formed. It will be observed that no matter where a cross section is taken on the head of my novel plunger, it will comprise space free from plunger material.

I prefer that the groove 13 have a depth which is substantially twice the length of the contact surface 11 with the inner wall of the barrel and that the sealing plug and plunger B be made entirely of soft flexible rubber, but these specific features are not necessarily limitations of my invention. It is to be noted that it is not essential nor even very important that the pressure exerted by the liquid on moving the plunger forward in the syringe should be the cause of contact between the surface 11 of the plunger head and the inside surface of the barrel; but what is important in my invention is that the annular ring 10 including the distal part 15 must be thick enough and strong enough to prevent a tendency to curl backward when the fluid is being expelled from the syringe and to exert sufficient force against the inside wall of the barrel to prevent leakage while the fluid in the syringe is being expelled therefrom or during jarring in transportation, and such thickness and strength will, of course, be dependent upon the resilience and other physical characteristics of the material of which the plunger is made which is preferably rubber. This is important since a jar which might exert no pressure on the fluid, say a jar from the side, and which consequently would have little or no effect on keeping the annular contact surface 11 against the inside wall of the barrel, would tend to have quite the opposite effect, namely, to make a break or opening so that fluid could leak from the front to the back of the plunger.

While certain features of the present invention are more or less specifically described, I wish it understood that various changes may be resorted to within the scope of the appended claims; similarly, that the materials and finishes of the several parts employed may be such as the manufacturer may decide or varying conditions or uses may demand.

Having thus described my invention, what I claim and desire to secure by Letters Patent is:

1. A combined container and syringe comprising a barrel and a soft, flexible, resilient, elastic member therewithin, said member having a forward portion, a rearward portion and an intermediate portion connecting said two first mentioned portions, the forward face of said forward portion having an annular groove therein extending through said forward portion and at least into said intermediate portion, the outer periphery of said rearward portion being substantially smaller than the interior of said barrel to form a manipulating shank, said forward portion being normally slightly larger than said interior to form a contact portion, said contact portion having a ring of contact with the interior of said barrel, the outer wall of said groove being at all points thereof a substantial distance away from said contact surface, said intermediate portion graduating in cross-section from that of said contact portion to that of said shank portion, all of said contact and intermediate portions being of a thickness sufficient to maintain said contact during shipment and storage and to prevent curling back to maintain said contact on pushing said member forwardly.

2. A combined container and syringe comprising: a barrel; and a soft, flexible, resilient, elastic plunger accommodated within said barrel, said plunger having a forward contact portion of a uniform and normally larger diameter than that of said barrel and merging into a rearwardly extending portion having a cross-sectional area somewhat smaller than that of said barrel, the forward face of said forward contact portion having an annular groove therein extending through said forward contact portion and at least into said rearwardly extending portion, the outer wall of said groove being at all points thereof a substantial distance away from the outer wall of said forward contact portion so that contact is maintained between said forward contact portion and said barrel during shipment and storage, and curling back of said contact portion is prevented on relative motion between the barrel and plunger.

ROBERT K. CUTTER.